(12) United States Patent
Tomas et al.

(10) Patent No.: US 9,273,363 B2
(45) Date of Patent: Mar. 1, 2016

(54) GENETIC LOCI ASSOCIATED WITH RESISTANCE OF CORN TO FIJIVIRUS

(75) Inventors: Adriana Tomas, Newark, DE (US);
Stanley Luck, Wilmington, DE (US);
Teresita Martin, Pergamino (AR);
Enrique Domingo Kreff, Pergamino (AR)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 259 days.

(21) Appl. No.: 13/877,461

(22) PCT Filed: Nov. 10, 2011

(86) PCT No.: PCT/US2011/060097
§ 371 (c)(1),
(2), (4) Date: Apr. 3, 2013

(87) PCT Pub. No.: WO2012/067925
PCT Pub. Date: May 24, 2012

(65) Prior Publication Data
US 2013/0212734 A1    Aug. 15, 2013

Related U.S. Application Data

(60) Provisional application No. 61/414,643, filed on Nov. 17, 2010.

(51) Int. Cl.
*C12Q 1/68* (2006.01)
*A01H 1/04* (2006.01)

(52) U.S. Cl.
CPC ............... *C12Q 1/6895* (2013.01); *A01H 1/04* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

| CN | 101849023 | 9/2010 |
|---|---|---|
| WO | 2009/058335 A1 | 5/2009 |
| WO | WO 2009/058335 A1 * | 5/2009 |
| WO | WO 2009/058335 A1 * | 7/2009 |

OTHER PUBLICATIONS

Lai et al., 2004, Genome Research 14: 1932-1937.*
GenBank sequence of *Zea mays* clone EL01N0442F12 with accession No. BT024143.1.*
Alexandrov et al., 2009, Plant Mol. Biol. 69: 179-194.*
GenBank sequence of *Zea mays* clone 328986 with accession No. EU969349.1.*
Bonamico et al., 2009, Maize Genomics Cooperation Newsletter 83: 42-44.*
Kreff et al., 2006, Journal of Basic & Applied Genetics 17: 41-50.*
Batley and Edwards, 2007, In: Association Mapping in Plants, pp. 95-102.*
M. A. Direnzo et al., Microsatellite markers linked to QTL for resistance to Mal de Rio Cuarto disease in *Zea mays* L., Journal of Agricultural Science, 2004, pp. 289-295, vol. 142.
Kreff et al., Journal of Basic and Applied Genetics, 2006, pp. 41-50, vol. 17.
National Center for Biotechnology Information GenBank GI No. 86306642, Accession No. DX359120.
Di Dianping et al., Journal of Agricultural University Henan, May 31, 2005, pp. 76-78, 103, vol. 28, No. 2.
International Search Report PCT/US2011/060097.
China Search Report.

* cited by examiner

*Primary Examiner* — David T Fox
*Assistant Examiner* — Bratislav Stankovic

(57) ABSTRACT

The invention relates to methods and compositions for identifying and/or selecting maize plants that have newly conferred resistance or enhanced resistance to, or are susceptible to, a Fijivirus, particularly Mal de Rio Cuarto Virus (MRCV) and/or Maize Rough Dwarf Virus (MRDV). The methods use molecular genetic markers to identify, select, and/or construct resistant plants or to identify and counter-select susceptible plants. Maize plants that display newly conferred resistance or enhanced resistance to a Fijivirus (or an infection or disease caused by the virus) that are generated by the methods of the invention are also a feature of the invention.

1 Claim, 6 Drawing Sheets

FIG. 1 Association between marker locus on chromosome 4 and MRCV resistance in a tropical subpopulation Arrows indicate top two significant marker-trait associations FIG. 2 Association between marker locus on chromosome 5 and MRCV resistance in a tropical subpopulation Arrow indicates significant marker trait association at marker locus PHM6921 (p-value = 6.6 E-05).

FIG. 3 Association between marker loci on chromosome 5 and MRCV resistance in a population of Argentinian inbreds Boxed region indicates marker loci significantly associated with MRCV resistance at a p-value of ≤ 0.001.

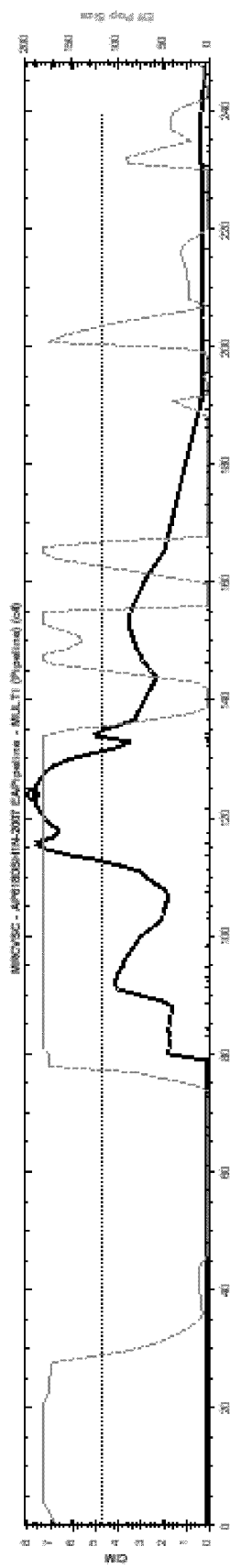
FIG. 4  QTL for MRCV resistance on chromosome 4
(mapped in the biparental population
PHFHH x FIG. 5  QTL for MRCV resistance on chromosome 5
(mapped in the biparental population
PHFHH x PHBNB)

FIG. 6 QTL for MRCV resistance on chromosome 5 (mapped in the F3 population derived from the biparental cross PHFNH x PHKV1)

GENETIC LOCI ASSOCIATED WITH RESISTANCE OF CORN TO FIJIVIRUS

CROSS REFERENCE TO RELATED APPLICATIONS

This application claims the benefit of U.S. Provisional Application No. 61/414,643, filed Nov. 17, 2010, the entire content of which is herein incorporated by reference.

FIELD OF THE INVENTION

The present disclosure relates to compositions and methods useful in creating or enhancing Fijivirus, particularly Mal de Rio Cuarto Virus and/or Maize Rough Dwarf Virus, resistance in plants.

BACKGROUND OF THE INVENTION

The disease caused by Mal de Rio Cuarto Virus (MRCV) is a major corn disease in Argentina, accounting for yield losses of greater than 70% in years of severe outbreak (Rodriguez P E et al. (1998) *Plant Dis.* 82:149-52). The disease is a member of Serogroup 2 of Fijivirus, which includes other viruses such as maize rough dwarf virus, rice black streaked dwarf virus, and pangola stunt virus (Uyeda I & Milne R G (1995) *Semin. Virol.* 6:85-88). The main vector for MRCV is *Delphacodes kuscheli*, but other *Delphacodes* species, such as *D. haywardi* and *D. tigrinus*, and *Toya propinqua* have been shown to carry the virus. The virus does not appear to be transmitted to progeny via seeds. Distéfano at al., Arch. Viral. 147:1699-1709 (2002), analyzed the MRCV sequence and proposed that it is a new Fijivirus species related to MRDV (Maize Rough Dwarf Virus). MRDV is found in several European countries (e.g., the Czech Republic, France, Italy, Norway, Spain, Sweden) and in China, while MRCV has been also detected in Uruguay (Omaghi J. A., Beviacqua J. E., Aguirrezabala D. A., March G. J. and Lenardón S. L. 1999. Detection of Mal de Rio Cuarto virus in Uruguay. Fitopatologia Brasileira 24: 471).

MRCV infection causes abnormal maize development and significantly reduces crop yields. The susceptible phenotype includes stunting, shortening of internodes, multiple ears with scattered grain, deformed tassel with no anthers, presence of small enations in the back of the leaves, reduced roots, cut and reduced leaves. Plants symptoms depend on phenological stage of the plant, plant genotype, and environment (Lenardón et al., “Virus del Mal de Rio Cuarto en maiz”, in Proyecto de Investigaciones en Fitovirologia (Lenardón ed.), 2:10 (1999). Most severe symptoms occur when infected at the coleoptile—first leaf stage.

In the severe MRCV outbreak of 1996-1997, over 300,000 hectares of maize in Argentina were affected, resulting in losses totaling approximately $120 million. Increased populations of *Delphacodes kuscheli* in 2006 apparently led to a reoccurrence of the viral disease in Argentinean corn plants, which significantly affected the 2007 harvesting. Susceptible genotypes were strongly affected by MRCV at the endemic region (Córdoba Province) and moderately affected at other maize regions.

The development of molecular genetic markers has facilitated mapping and selection of agriculturally important traits in maize, and QTL for resistance to Mal de Rio Cuarto virus in maize have been identified. Microsatellite markers on maize chromosomes 1 and 8 were found to be linked to QTL for resistance to Mal de Rio Cuarto disease (DiRenzo et al. (2004) *J. Agricultural Science* 142:289-295), and another major QTL conferring resistance of corn to a Fijivirus was identified on chromosome 2 (WO2009/058335). In addition, QTL conferring resistance to Mal de Rio Cuarto Virus in maize were mapped to the short and long arms of chromosome 1, and chromosomes 4, 8, and 10 (Kreff et al. (2006) Journal of Basic and Applied Genetics 17:41-50).

Selection through the use of molecular markers associated with resistance to MRCV infection has the advantage of permitting at least some selection based solely on the genetic composition of the progeny. Moreover, resistance to MRCV infection can be determined very early on in the plant life cycle, even as early as the seed stage. The increased rate of selection that can be obtained through the use of molecular markers associated with the resistance trait means that plant breeding for resistance to MRCV infection can occur more rapidly, thereby generating commercially acceptable resistant plants in a relatively short amount of time. Thus, it is desirable to provide compositions and methods for identifying and selecting maize plants with enhanced resistance to MRCV infection. These plants can be used in breeding programs to generate high-yielding hybrids with resistance to MRCV infection.

SUMMARY

Compositions and methods for identifying and selecting maize plants with enhanced resistance to the disease caused by Mal de Rio Cuarto Virus (MRCV) or a related Fijivirus are provided.

In one embodiment, methods of identifying and/or selecting a maize plant with enhanced resistance to MRCV infection are provided. In these methods, the presence of at least one marker allele is detected and a maize plant with enhanced resistance to MRCV infection is identified and/or selected. The marker allele can include any marker allele that is linked to and associated with: a haplotype consisting of a “G” at position 324, a “C” at position 345, a “G” at position 504, and an “A” at position 565, relative to SEQ ID NO:44; a haplotype consisting of an “A” at position 85, a “C” at position 344, and an “A” at position 355 relative to SEQ ID NO:42; or a haplotype consisting of a “G” at position 58, an insertion at position 61, a “C” at position 70, a “C” at position 85, a “T” at position 90, a “G” at position 194, and an “A” at position 287, relative to SEQ ID NO:43.

In other embodiments, the marker allele can be linked to a haplotype consisting of a “G” at position 324, a “C” at position 345, a “G” at position 504, and an “A” at position 565, relative to SEQ ID NO:44; a haplotype consisting of an “A” at position 85, a “C” at position 344, and an “A” at position 355 relative to SEQ ID NO:42; or a haplotype consisting of a “G” at position 58, an insertion at position 61, a “C” at position 70, a “C” at position 85, a “T” at position 90, a “G” at position 194, and an “A” at position 287, relative to SEQ ID NO:43 by 30 cM, 25, 20, 15, 10, 9, 8, 7, 6, 5, 4, 3, 2, 1, 0.9, 0.8, 0.7, 0.6, 0.5, 0.4, 0.3, 0.2, or 0.1 cM on a single meiosis map.

In another embodiment, methods of identifying and/or selecting a maize plant with enhanced resistance to MRCV infection are provided in which a haplotype is detected and a maize plant with enhanced resistance to MRCV infection is identified and/or selected. The haplotype can include: a haplotype comprising a “G” at position 324, a “C” at position 345, a “G” at position 504, and an “A” at position 565, relative to SEQ ID NO:44; a haplotype comprising an “A” at position 85, a “C” at position 344, and an “A” at position 355 relative to SEQ ID NO:42; a haplotype comprising a “G” at position 58, an insertion at position 61, a “C” at position 70, a “C” at position 85, a “T” at position 90, a “G” at position 194, and an "A" at position 287, relative to SEQ ID NO:43; or a combination of any of the haplotypes described above.

In another embodiment, methods for identifying and/or selecting maize plants with enhanced resistance to MRCV infection by detecting a marker allele or haplotype associated with the enhanced resistance to MRCV infection in the germplasm of the maize plant. The haplotype can comprise alleles at one or more marker loci, wherein the one or more marker loci are found within the interval on chromosome 4 comprising and flanked by:

i. PHM1718 and PHM8008; and ii. PHM669 and PHM8008.

The haplotype can also be selected from the group consisting of: a haplotype comprising a "G" at position 324, a "C" at position 345, a "G" at position 504, and an "A" at position 565, relative to SEQ ID NO:44; a haplotype comprising an "A" at position 85, a "C" at position 344, and an "A" at position 355 relative to SEQ ID NO:42; a haplotype comprising a "G" at position 58, an insertion at position 61, a "C" at position 70, a "C" at position 85, a "T" at position 90, a "G" at position 194, and an "A" at position 287, relative to SEQ ID NO:43; or a combination of any of the haplotypes described above.

In another embodiment, methods of identifying and/or selecting maize plants with enhanced resistance to MRCV infection are obtained in which maize plants comprising within their genomes a haplotype comprising a "G" at position 324, a "C" at position 345, a "G" at position 504, and an "A" at position 565, relative to SEQ ID NO:44; a haplotype comprising an "A" at position 85, a "C" at position 344, and an "A" at position 355 relative to SEQ ID NO:42; a haplotype comprising a "G" at position 58, an insertion at position 61, a "C" at position 70, a "C" at position 85, a "T" at position 90, a at position 194, and an "A" at position 287, relative to SEQ ID NO:43; or any combination of said haplotypes, can be crossed to other maize plants; and the progeny can be evaluated for the presence or absence of the one or more haplotypes, thereby identifying and/or selecting progeny plants with enhanced resistance to MRCV infection.

In another embodiment, methods for identifying and/or selecting maize plants with enhanced resistance to MRCV infection by detecting a marker locus in the genome of the maize plant using the sequence of the marker locus, a portion of the sequence of the marker locus, or a complement of the sequence of the marker locus, or of a portion thereof, as a marker probe, are provided. The marker probe hybridizes under stringent conditions to the contiguous DNA between and including SEQ ID NO:71, or a nucleotide sequence that is 95% identical to SEQ ID NO:71 based on the Clustal V method of alignment, and SEQ ID NO:50, or a nucleotide sequence that is 95% identical to SEQ ID NO:50 based on the Clustal V method of alignment, and the marker locus comprises at least one allele that is associated with the enhanced resistance to MRCV infection.

In another embodiment, methods for identifying and/or selecting maize plants with enhanced resistance to MRCV infection by detecting at least one marker allele associated with the enhanced resistance in the germplasm of a maize plant are provided. The marker locus can be selected from any of the following marker loci: PHM15741, PHM12093, PHM15051, PHM8091, PHM6248, PHM9452, PHM12615, PHM5713, PHM6921, PHM1683, and PHM17281; as well as any other marker that is linked to these markers. The marker locus can also be found within any of the following intervals on chromosome 5 comprising and flanked by:

i. PHM12615 and PHM9452;

ii. PHM12615 and PHM17281;

ii. PHM12615 and PHM1683; and iv. PHM15741 and PHM9452.

The marker locus comprises at least one allele that is associated with enhanced resistance to MRCV infection.

In another embodiment, methods for identifying and/or selecting maize plants with enhanced resistance to MRCV infection by detecting a haplotype in the germplasm of the maize plant that is associated with enhanced resistance to MRCV infection are provided. The haplotype comprises alleles at one or more marker loci, wherein the one or more marker loci are found within the interval on chromosome 5 comprising and flanked by:

i. PHM12615 and PHM9452;

iv. PHM12615 and PHM17281;

v. PHM12615 and PHM1683; and vi. PHM15741 and PHM9452.

In another embodiment, methods of identifying and/or selecting plants with enhanced resistance to MRCV infection are provided. In one aspect, a first maize plant is obtained that has at least one allele of a marker locus wherein the allele is associated with the enhanced resistance. The marker locus can be found within the interval on chromosome 5 comprising and flanked by:

PHM12615 and PHM9452;

ii. PHM12615 and PHM17281;

iii. PHM12615 and PHM1683; and iv. PHM15741 and PHM9452.

The first maize plant can then be crossed to a second maize plant, and the progeny plants resulting from the cross can be evaluated for the allele of the first maize plant. Progeny plants that possess the allele of the first maize plant can be selected as having enhanced resistance to MRCV infection.

Additionally, maize plants identified or selected by the methods described above are of interest, as are progeny of maize plants identified or selected by the methods described above.

BRIEF DESCRIPTION OF DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows a peak of significant marker trait associations on chromosome 4 within the tropical subpopulation. These results were obtained from the structured association analysis on the set of 475 lines described in Example 2.

FIG. 2 shows a peak of significant marker trait associations on chromosome within the tropical subpopulation. These results were obtained from the structured association analysis on the set of 475 lines described in Example 2.

FIG. 3 shows a peak of significant marker trait associations on chromosome 5 for a set of Argentinean inbreds (Example 3).

FIG. 4 shows a graph depicting a QTL for MRCV resistance on chromosome 4 in the PHFHH×PHBNB population.

FIG. 5 shows a graph depicting a QTL for MRCV resistance on chromosome 5 in the PHFHH×PHBNB population.

FIG. 6 shows a graph depicting a QTL for MRCV resistance on chromosome 5 in an F3 population derived from the biparental cross PHFNHxPHKV1.

SEQ ID NO:1 is the PHM1718 external forward primer.
SEQ ID NO:2 is the PHM1718 internal forward primer.
SEQ ID NO:3 is the PHM1718 internal reverse primer.
SEQ ID NO:4 is the PHM1718 external reverse primer.
SEQ ID NO:5 is the PHM669 external forward primer.
SEQ ID NO:6 is the PHM669 internal forward primer.
SEQ ID NO:7 is the PHM669 internal reverse primer.
SEQ ID NO:8 is the PHM669 external reverse primer.
SEQ ID NO:9 is the PHM11786 external forward primer.
SEQ ID NO:10 is the PHM11786 internal forward primer.
SEQ ID NO:11 is the PHM11786 internal reverse primer.
SEQ ID NO:12 is the PHM11786 external reverse primer.
SEQ ID NO:13 is the PHM8008 external forward primer.
SEQ ID NO:14 is the PHM8008 internal forward primer.
SEQ ID NO:15 is the PHM8008 internal reverse primer.
SEQ ID NO:16 is the PHM8008 external reverse primer.
SEQ ID NO:17 is the PHM15741 external forward primer.
SEQ ID NO:18 is the PHM15741 internal forward primer.
SEQ ID NO:19 is the PHM15741 internal reverse primer.
SEQ ID NO:20 is the PHM15741 external reverse primer.
SEQ ID NO:21 is the PHM12093 external forward primer.
SEQ ID NO:22 is the PHM12093 internal forward primer.
SEQ ID NO:23 is the PHM12093 internal reverse primer.
SEQ ID NO:24 is the PHM12093 external reverse primer.
SEQ ID NO:25 is the PHM15051 external forward primer,
SEQ ID NO:26 is the PHM15051 internal forward primer.
SEQ ID NO:27 is the PHM15051 internal reverse primer.
SEQ ID NO:28 is the PHM15051 external reverse primer.
SEQ ID NO:29 is the PHM8091 external forward primer.
SEQ ID NO:30 is the PHM8091 internal forward primer.
SEQ ID NO:31 is the PHM8091 internal reverse primer.
SEQ ID NO:32 is the PHM8091 external reverse primer.
SEQ ID NO:33 is the PHM6248 external forward primer.
SEQ ID NO:34 is the PHM6248 internal forward primer.
SEQ ID NO:35 is the PHM6248 internal reverse primer.
SEQ ID NO:36 is the PHM6248 external reverse primer.
SEQ ID NO:37 is the PHM9452 external forward primer.
SEQ ID NO:38 is the PHM9452 internal forward primer.
SEQ ID NO:39 is the PHM9452 internal reverse primer.
SEQ ID NO:40 is the PHM9452 external reverse primer.
SEQ ID NO:41 is the PHM1718 reference sequence.
SEQ ID NO:42 is the PHM669 reference sequence.
SEQ ID NO:43 is the PHM11786 reference sequence.
SEQ ID NO:44 is the PHM8008 reference sequence.
SEQ ID NO:45 is the PHM15741 reference sequence.
SEQ ID NO:46 is the PHM12093 reference sequence.
SEQ ID NO:47 is the PHM15051 reference sequence.
SEQ ID NO:48 is the PHM8091 reference sequence.
SEQ ID NO:49 is the PHM6248 reference sequence.
SEQ ID NO:50 is the PHM9452 reference sequence.
SEQ ID NO:51 is the PHM12615 external forward primer.
SEQ ID NO:52 is the PHM12615 internal forward primer.
SEQ ID NO:53 is the PHM12615 internal reverse primer.
SEQ ID NO:54 is the PHM12615 external reverse primer.
SEQ ID NO:55 is the PHM5713 external forward primer.
SEQ ID NO:56 is the PHM5713 internal forward primer.
SEQ ID NO:57 is the PHM5713 internal reverse primer,
SEQ ID NO:58 is the PHM5713 external reverse primer.
SEQ ID NO:59 is the PHM6921 external forward primer.
SEQ ID NO:60 is the PHM6921 internal forward primer.
SEQ ID NO:61 is the PHM6921 internal reverse primer.
SEQ ID NO:62 is the PHM6921 external reverse primer.
SEQ ID NO:63 is the PHM1683 external forward primer.
SEQ ID NO:64 is the PHM1683 internal forward primer,
SEQ ID NO:65 is the PHM1683 internal reverse primer.
SEQ ID NO:66 is the PHM1683 external reverse primer.
SEQ ID NO:67 is the PHM17281 external forward primer.
SEQ ID NO:68 is the PHM17281 internal forward primer.
SEQ ID NO:69 is the PHM17281 internal reverse primer.
SEQ ID NO:70 is the PHM17281 external reverse primer.
SEQ ID NO:71 is the PHM12615 reference sequence.
SEQ ID NO:72 is the PHM5713 reference sequence.
SEQ ID NO:73 is the PHM6921 reference sequence.
SEQ ID NO:74 is the PHM1683 reference sequence.
SEQ ID NO:75 is the PHM17281 reference sequence.

DETAILED DESCRIPTION

The identification and selection of maize plants that have enhanced resistance to Mal de Rio Cuarto Virus (MRCV), or the disease or infection caused by the virus, through the use of marker assisted selection can provide an effective and environmentally friendly approach to overcoming losses caused by this disease. The present invention provides maize marker loci that demonstrate statistically significant co-segregation with MRCV. Detection of these loci or additional linked loci can be used in marker assisted maize breeding programs to produce resistant plants, or plants with enhanced resistance to MRCV or a related fijivirus, or an infection or disease caused by MRCV or a related fijivirus. The following definitions are provided as an aid to understand this invention.

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. Public assemblies can be found using the Maize Genome Browser, which is publicly available on the internet.

An allele is "associated with" a trait when it is part of or linked to a DNA sequence or allele that affects the expression of the trait. The presence of the allele is an indicator of how the trait will be expressed.

A "BAC", or bacterial artificial chromosome, is a cloning vector derived from the naturally occurring F factor of *Escherichia coli*, which itself is a DNA element that can exist as a circular plasmid or can be integrated into the bacterial chromosome. BACs can accept large inserts of DNA sequence. In maize, a number of BACs each containing a large insert of maize genomic DNA from maize inbred line B73, have been assembled into contigs (overlapping contiguous genetic fragments, or "contiguous DNA"), and this assembly is available publicly on the Internet.

A BAC fingerprint is a means of analyzing similarity between several DNA samples based upon the presence or absence of specific restriction sites (restriction sites being nucleotide sequences recognized by enzymes that cut or "restrict" the DNA). Two or more BAC samples are digested with the same set of restriction enzymes and the sizes of the fragments formed are compared, usually using gel separation.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw at al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coned DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

The term "contiguous DNA" refers to an uninterrupted stretch of genomic DNA represented by partially overlapping pieces or contigs.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

A plant referred to herein as "diploid" has two sets (genomes) of chromosomes.

The phrase "disease caused by Mal de Rio Cuarto Virus" or "disease caused by MRCV" refers to the plant disease caused by an infection of the plant with MRCV or a related Fijivirus.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

An "elite line" is any line that has resulted from breeding and selection for superior agronomic performance.

"Enhanced resistance" in a maize plant to MRCV, or the infection or disease caused by MRCV, is an indication that the maize plant is less affected with respect to yield and/or survivability or other relevant agronomic measures, upon introduction of the causative agents of that disease. Resistance is a relative term, indicating that the infected plant produces better yield of maize than another, similarly treated, more susceptible plant. That is, the conditions cause a reduced decrease in maize survival and/or yield in a resistant maize plant, as compared to a susceptible maize plant.

An "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

A "favorable allele" is the allele at a particular locus that confers, or contributes to, an agronomically desirable phenotype, e.g., resistance to MRCV, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic adds that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic adds used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

The term "heterogeneity" is used to indicate that individuals within the group differ in genotype at one or more specific loci.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.*

80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maizeGDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps or physical maps, cleaned date, or the use of new algorithms.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meioses (e.g. an $F_2$); the IBM2 maps consist of multiple meioses). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9 e/o, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A. Theor. Appl. Genet. 38:226-231 (1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

"Maize" refers to a plant of the *Zea mays* L. ssp. *mays* and is also known as "corn".

The term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (eg a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected eg via DNA sequencing, FOR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology have the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus,

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA between 2 or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indictor that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered significant or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hybrid Marker', followed by a number that is specific to the sequence from which it was designed, followed by a "." or a "-" and then a suffix that is specific to the DNA polymorphism. A marker version can also follow (A, B, C etc) that denotes the version of the marker designed to that specific polymorphism.

The term "progeny" refers to the offspring generated from a cross.

A "progeny plant" is a plant generated from a cross between two plants.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

One of skill will appreciate that "resistance" to MRCV varies widely, can represent a spectrum of more resistant or less resistant phenotypes, and can vary depending on the severity of the infection. However, by simple observation, one of skill can determine the relative resistance or susceptibility of different plants, plant lines or plant families to MRCV, and furthermore, will also recognize the phenotypic gradations of "resistant" (an exemplary scoring system is presented in Example 1 below).

A "topcross test" is a test performed by crossing each individual (e.g. a selection, inbred line, clone or progeny individual) with the same pollen parent or "tester", usually a homozygous line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often; 50% formamide, 5×SSC, and 1% SOS, incubating at 42° C., or, 5×SSC, 1 SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Turning now to the embodiments:

Resistance to the Disease Caused by Mal De Rio Cuarto Virus (MRCV)

The disease caused by Mal de Rio Cuarto Virus (MRCV) is a devastating disease of maize caused by species of Fijivirus. The identification of molecular markers and alleles of molecular markers that are associated with MRCV resistance allows selection for resistance based solely on the genetic composition of the progeny. Methods for identifying and selecting maize plants with enhanced resistance to MRCV, or the disease or infection caused by Mal de Rio Cuarto Virus (MRCV), through the evaluation of genetic composition (as assessed using molecular markers and their alleles) are presented herein.

Genetic Mapping

It has been recognized for quite some time that specific genetic loci correlating with particular phenotypes, such as resistance to the disease caused by Mal de Rio Cuarto Virus (MRCV), can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as resistance to the disease caused by Mal de Rio Cuarto Virus (MRCV). The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides maize marker loci that demonstrate statistically significant co-segregation with resistance to the disease caused by Mal de Rio Cuarto Virus (MRCV), as determined by traditional linkage analysis. Detection of these loci or additional linked loci can be used in marker assisted maize breeding programs to produce plants with enhanced resistance to MRCV infection.

Marker Compositions

Markers associated with resistance to the disease caused by Mal de Rio Cuarto Virus (MRCV) are identified herein. The methods involve detecting the presence of one or more marker alleles associated with the enhanced resistance in the germplasm of a maize plant. The maize plant can be a hybrid or inbred.

For the QTL identified on chromosome 4, the marker locus can be selected from any of the marker loci provided in Table 2, including the PHM markers PHM1718, PHM669, PHM11786, and PHM8008; as well as any other marker linked to these markers (linked markers can be determined from the MaizeGDB resource).

For the QTL identified on chromosome 5, the marker locus can be selected from any of the marker loci provided in Tables 2 and 3, including the PHM markers PHM15741, PHM12093, PHM15051, PHM8091, PHM6248, PHM9452, PHM12615, PHM5713, PHM6921, PHM1683, and PHM17281; as well as any other marker linked to these markers (linked markers can be determined from the MaizeGDB resource).

Physical Map Locations of QTLs

The genetic elements or genes located on a contiguous linear span of genomic DNA on a single chromosome are physically linked.

In the association analysis, PHM1718 and PHM8008 were found to delineate a QTL for resistance to MRCV on chromosome 4. The positions of PHM1718 and PHM8008 are based on the PHB genetic map, which order the markers as described in Table 1. However, the public physical map derived from the public maize line B73 shows the following order: PHM669, PHM1718, PHM11786, and PHM8008. Any polynucleotide that assembles to the contiguous DNA between and including SEQ ID NO:41 (the reference sequence for PHM1718), or a nucleotide sequence that is 95% identical to SEQ ID NO:41 based on the Clustal V method of alignment, and SEQ ID NO:44 (the reference sequence for PHM8008), or a nucleotide sequence that is 95% identical to SEQ ID NO:44 based on the Clustal V method of alignment, can house marker loci that are associated with the MRCV resistance trait. Additionally, any polynucleotide that assembles to the contiguous DNA between and including SEQ ID NO:42 (the reference sequence for PHM669), or a nucleotide sequence that is 95% identical to SEQ ID NO:42 based on the Clustal V method of alignment, and SEQ ID NO:44 (the reference sequence for PHM8008), or a nucleotide sequence that is 95% identical to SEQ ID NO:44 based on the Clustal V method of alignment, can house marker loci that are associated with the MRCV resistance trait.

In the association mapping analysis performed on the set of 475 lines, PHM12615 and PHM17281 were found to delineate a QTL for resistance to MRCV on chromosome 5. The positions of PHM12615 and PHM17281 are based on the PHB genetic map, which order the markers as described in Table 2. However, the public physical map derived from the public maize line B73 shows the following order: PHM12615, PHM5713, PHM6921, PHM17281, and PHM1683. Any polynucleotide that assembles to the contiguous DNA between and including SEQ ID NO:71 (the reference sequence for PHM12615), or a nucleotide sequence that is 95% identical to SEQ NO:71 based on the Clustal V method of alignment, and SEQ ID NO:75 (the reference sequence for PHM17281), or a nucleotide sequence that is 95% identical to SEQ ID NO:75 based on the Clustal V method of alignment, can house marker loci that are associated with the MRCV resistance trait. Additionally, any polynucleotide that assembles to the contiguous DNA between and including SEQ ID NO:71 (the reference sequence for PHM12615), or a nucleotide sequence that is 95% identical to SEQ ID NO:71 based on the Clustal V method of alignment, and SEQ ID NO:74 (the reference sequence for PHM1683), or a nucleotide sequence that is 95% identical to SEQ ID NO:74 based on the Clustal V method of alignment, can house marker loci that are associated with the MRCV resistance trait.

In the association mapping analysis performed on the set of Argentinean inbreds, PHM15741 and PHM9452 were found to delineate a QTL for resistance to MRCV on chromosome 5. Any polynucleotide that assembles to the contiguous DNA between and including SEQ ID NO:45 (the reference sequence for PHM15741), or a nucleotide sequence that is 95% identical to SEQ ID NO:45 based on the Clustal V method of alignment, and SEQ ID NO:50 (the reference sequence for PHM9452), or a nucleotide sequence that is 95% identical to SEQ ID NO:50 based on the Clustal V method of alignment, can house marker loci that are associated with the MRCV resistance trait.

The larger QTL interval on chromosome 5 encompassing one or more QTL is bounded by PHM12615 and PHM9452. Any polynucleotide that assembles to the contiguous DNA between and including SEQ ID NO:71 (the reference sequence for PHM12615), or a nucleotide sequence that is 95% identical to SEQ ID NO:71 based on the Clustal V method of alignment, and SEQ ID NO:50 (the reference sequence for PHM9452), or a nucleotide sequence that is 95% identical to SEQ ID NO:50 based on the Clustal V method of alignment, can house marker loci that are associated with the MRCV resistance trait.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with resistance to MRCV, it is important to note that the marker locus is not necessarily responsible for the expression of the MRCV resistance phenotype. For example, it is not a requirement that the marker polynucleotide sequence be part of a gene that imparts enhanced resistance to MRCV, or the disease or infection caused by MRCV (for example, be part of the gene open reading frame). The association between a specific marker allele and the enhanced MRCV resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

For the QTL on chromosome 4, markers listed in Table 1 can be used to predict the state of the MRCV resistance trait in a maize plant. This includes any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM of the PHM markers PHM1718, PHM669, PHM11786, and PHM8008.

For the QTL on chromosome 5, markers listed in Tables 2 and 3 can be used to predict the state of the MRCV resistance trait in a maize plant. This includes any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM of the PHM markers PHM15741, PHM12093, PHM15051, PHM8091, PHM6248, PHM9452, PHM12615, PHM5713, PHM6921, PHM1683, and PHM17281.

Chromosomal Intervals

Chromosomal intervals that correlate with resistance to MRCV are provided. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for MRCV resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The intervals described below show a clustering of markers that co-segregate with resistance to MRCV. This clustering of markers occurs in relatively small domains on the chromosomes, indicating the presence of one or more QTL in those chromosome regions. The interval was drawn to encompass markers that co-segregate with MRCV resistance. The intervals are defined by the markers on their termini, where the interval encompasses markers that map within the interval as well as the markers that define the termini. An interval described by the terminal markers that define the endpoints of the interval will include the terminal markers and any marker localizing within that chromosomal domain, whether those markers are currently known or unknown.

For the OIL on chromosome 4, an interval may be defined by and includes markers PHM1718 and PHM8008 or PHM669 and PHM8008. Any marker located within these intervals can find use as a marker for resistance to MRCV, For the QTL on chromosome 5, any marker located within any of the following intervals defined by and including:
  i. PHM12615 and PHM9452;
  ii. PHM12615 and PHM17281;
  iii. PHM12615 and PHM1683; and
  iv. PHM15741 and PHM8452
can find use as a marker for resistance to MRCV.

Chromosomal intervals can also be defined by markers that are linked to (show linkage disequilibrium with) a QTL marker, and $r^2$ is a common measure of linkage disequilibrium (LD) in the context of association studies. If the $r^2$ value of LD between a chromosome 5 marker locus lying within the interval of PHM12615 and PHM9452, for example, and another chromosome 5 marker locus in close proximity is greater than 1/3 (Ardlie et al., Nature Reviews Genetics 3:299-309 (2002)), the loci are in linkage disequilibrium with one another.

Marker Alleles and Haplotypic Combinations

A marker of the invention can also be a combination of alleles at one or more marker loci, often referred to as a haplotype.

The following chromosome 4 haplotypes are shown herein to be linked to enhanced resistance to MRCV infection and can be used in marker assisted selection to select for maize plants with enhanced resistance to MRCV infection:
 a) a haplotype comprising a "G" at position 324, a "C" at position 345, a "G" at position 504, and an "A" at position 565, relative to SEQ ID NO:44;
 b) a haplotype comprising an "A" at position 85, a "C" at position 344, and an "A" at position 355 relative to SEQ ID NO:42; and
 c) a haplotype comprising a "G" at position 58, an insertion at position 61, a "C" at position 70, a "C" at position 85, a "T" at position 90, a "G" at position 194, and an "A" at position 287, relative to SEQ ID NO:43

Any of the above haplotypes can be used alone or in combination to identify and select plants with enhanced resistance to MRCV infection.

The skilled artisan would expect that there might be additional polymorphic sites at marker loci in and around the chromosome 5 and chromosome 4 markers identified herein, wherein one or more polymorphic sites is in linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young at al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) Am J Hum Genet. 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Diol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), Invader®. (Third Wave Technologies) and Invader Plus®, SnapShot®. (Applied Biosystems), Taqman®. (Applied Biosystems) and Beadarrays®. (Illumina).

A number of SNPs together within a sequence, or across linked sequences, can be used to describe a haplotype for any particular genotype (Ching et al. (2002), *BMC Genet*. 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with enhanced resistance to MRCV infection, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene, See, for example, WO2003054229. Using automated high throughput marker detection platforms known to those of ordinary skill in the art makes this process highly efficient and effective.

Many of the PHM markers can readily be used as FLP markers to select for the gene loci on chromosomes 4 and 5, owing to the presence of insertions/deletion polymorphisms. Primers for the PHM markers can also be used to convert these markers to SNP or other structurally similar or functionally equivalent markers (SSRs, CAPs, indels, etc), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with a phenotype, such as resistance to MRCV. Such markers are presumed to map near a gene or genes that give the plant its MRCV resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with enhanced resistance to MRCV infection can be selected for by detecting one or more marker alleles, and in addition, progeny plants derived from those plants can also be selected. Hence, a plant containing a desired genotype in a given chromosomal region (i.e. a genotype associated with enhanced resistance to MRCV infection) is obtained and then crossed to another plant. The progeny of such a cross would then be evaluated genotypically using one or more markers and the progeny plants with the same genotype in a given chromosomal region would then be selected as having enhanced resistance to MRCV infection.

Markers identified herein could be used in MAS to select maize plants with enhanced resistance to MRCV infection.

Haplotypes can also be used in MAS to introduce enhanced resistance to MRCV infection into susceptible maize lines or varieties. The following chromosome 4 haplotypes can be used in marker assisted selection to select for maize plants with enhanced resistance to MRCV infection:

a) a haplotype comprising a "G" at position 324, a "C" at position 345, a "G" at position 504, and an "A" at position 565, relative to SEQ ID NO:44;

b) a haplotype comprising an "A" at position 85, a "C" at position 344, and an "A" at position 355 relative to SEQ ID NO:42; or c) a haplotype comprising a "G" at position 58, an insertion at position 61, a "C" at position 70, a "C" at position 85, a "T" at position 90, a "G" at position 194, and an "A" at position 287, relative to SEQ ID NO:43.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Characterizing the Reaction to MRCV Infection

Maize lines can be characterized based on their degree of resistance or susceptibility to MRCV infection. A scale from one to nine can be used in which "1" refers to highly susceptible plants and "9" refers to highly resistant plants. In this scale, scores 1-3 indicate that most plants show severe dwarfism, severe internode shortening, poor or no ear development, or premature death; scores 4-6 indicate that most plants show only enations and/or mild internode shortening with very few plants showing severe symptoms; and scores 7-9 indicate highly resistant plants with no symptoms or few enations, Disease scores are usually taken at locations with natural infection. Controls, or lines with well known reactions to MRCV infection, are included in the experiments to gauge disease pressure at any particular location. If a location is deemed to have enough disease pressure, disease scores are collected typically after flowering.

Example 2

Association Mapping Analysis in a Set of 475 Lines

An association mapping strategy was undertaken to identify markers associated with MRCV resistance in maize. In this association analysis, a collection of 475 maize lines was analyzed by DNA sequencing at 4,000-10,000 genes (genetic loci). The lines encompassed elite germplasm, commercially released cultivars, and other public varieties. The maize lines were phenotyped as described in Example I. A combination of disease scores was used in the analysis, including scores obtained in the field in 2006 and consensus historical scores taken across several locations and several years.

A structure-based association analysis was conducted using standard association mapping methods where the population structure is controlled using marker data. The model-based cluster analysis software, Structure, developed by Pritchard et al. was used with haplotype data for 880 elite maize inbreds at two hundred markers to estimate admixture coefficients and assign the inbreds to seven subpopulations (J. K. Pritchard, M. Stephens and P. J. Donnelly (2000) "Inference of population structure using multilocus genotype data," Genetics 155:945-959). This reduces the occurrence of false positives that can arise due to the effect of population structure on association mapping statistics. Kuiper's statistic for testing whether two distributions are the same is used to test a given marker for association between haplotype and phenotype in a given subpopulation (W. H. Press, S. A. Teukolsky, W. T. Vetterling, B. P. Flannery, 2002; Numerical Recipes in C, second edition, Cambridge University Press, NY).

A peak of significant marker trait associations was identified on chromosome 4 (FIG. 1) within a tropical subpopulation. There were 80 lines assigned by the model-based cluster analysis software, Structure, to this tropical subpopulation. The marker that showed the most significant association with MRCV resistance was PHM8008 (p-value=$9.4 \times 10^{-5}$) located at position 136.03 on the internally derived genetic map (FHB). In addition, three other markers were significantly associated with MRCV resistance at a p-value≤0.01 in the tropical subpopulation. Table 1 shows the chromosome 4 markers significantly associated with MRCV resistance at p-value≤0.01.

TABLE 1

Chromosome 4 Markers Significantly Associated with MRCV Resistance at p-value ≤0.01 in the Tropical Subpopulation

| Marker Name | Relative map position (cM) on PHB map | p-Value | Primers | Reference sequence |
|---|---|---|---|---|
| PHM1718 | 125.34 | 9.3E−03 | SEQ ID NOs: 1-4 | SEQ ID NO: 41 |
| PHM669 | 126.01 | 2.0E−04 | SEQ ID NOs: 5-8 | SEQ ID NO: 42 |
| PHM11786 | 131.4 | 8.4E−03 | SEQ ID NOs: 9-12 | SEQ ID NO: 43 |
| PHM8008 | 136.03 | 9.4E−05 | SEQ ID NOs: 13-16 | SEQ ID NO: 44 |

A PHM8008 haplotype comprising a "G" at position 324, a "C" at position 345, a "G" at position 504, and an "A" at position 565, relative to the PHM8008 reference sequence (SEQ ID NO:44), was identified as the haplotype that led to the identification of a significant marker trait association at PHM8008. A review of the lines in the study and their respective phenotypes showed that this haplotype was associated with lines having enhanced resistance to MRCV infection (a median MRCV score of 7).

A PHM669 haplotype consisting of: a "G" at position 85, a "C" at position 344, and a "T" at position 355, relative to the PHM669 reference sequence (SEQ ID NO:42), was identified as the haplotype that led to the identification of a significant marker trait association at PHM669. A review of the lines in the study and their respective phenotypes showed that this haplotype was associated with more susceptible lines (a median MRCV score of 3). Lines having enhanced resistance to MRCV infection had a PHM669 haplotype consisting of: an "A" at position 85, a "C" at position 344, and an "A" at position 355 relative to the PHM669 reference sequence (SEQ ID NO:42) and a median MRCV score of 6.5.

A PHM11786 haplotype consisting of a "G" at position 58, an insertion at position 61, a "C" at position 70, a "C" at position 85, a "T" at position 90, a "G" at position 194, and an "A" at position 287, relative to the PHM11786 reference sequence (SEQ ID NO:43), was identified as the haplotype that led to the identification of a significant marker trait association at PHM11786. A review of the lines in the study and their respective phenotypes showed that this haplotype was associated with lines having enhanced resistance to MRCV infection (median MRCV score of 5).

A peak of significant marker trait associations was also identified on chromosome 5 (FIG. 2) within the same tropical subpopulation as described above. The most associated markers are shown in Table 2, and the marker that showed the most significant association with MRCV resistance was PHM6921 (p-value=$6.6\times10^{-5}$) located at position 90.13 of the internally derived genetic map (PHB).

TABLE 2

Chromosome 5 Markers Significantly Associated with MRCV Resistance at p-value ≤0.01 in the Tropical Subpopulation

| Marker Name | Relative map position (cM) on PHB map | p-Value | Primers | Reference Sequence |
|---|---|---|---|---|
| PHM12615 | 84.28 | 9.0E−04 | SEQ ID NOs: 51-54 | SEQ ID NO: 71 |
| PHM5713 | 84.89 | 8.2E−04 | SEQ ID NOs: 55-58 | SEQ ID NO: 72 |
| PHM6921 | 90.13 | 6.6E−05 | SEQ ID NOs: 59-62 | SEQ ID NO: 73 |
| PHM1683 | 92.94 | 9.4E−04 | SEQ ID NOs: 63-66 | SEQ ID NO: 74 |
| PHM17281 | 93.98 | 6.6E−04 | SEQ ID NOs: 67-70 | SEQ ID NO: 75 |

In Tables 1 and 2, positions are given in cM, with position zero being the first (most distal from the centromere) marker known at the beginning of the chromosome. The map positions are not absolute and represent an estimate of map position based on the internally derived genetic map (PHB).

Example 3

Association Mapping Analysis in a Set of Argentinian Inbreds

Another association mapping strategy was undertaken to identify markers associated with MRCV resistance in maize. In this study, a collection of 81 maize lines was analyzed by DNA sequencing at 4000-10000 genes (genetic loci). The collection encompassed elite germplasm of the Pioneer Hi-Bred Intl breeding program in Argentina, and the lines were phenotyped as described in Example 1. Phenotypic data was available for only 40 of the 81 lines. For the purpose of this analysis, the lines were considered as one subpopulation. A peak of significant marker trait associations was identified on chromosome 5 (FIG. 3) and encompassed the markers listed in Table 3. The most associated marker was PHM12093 (p-value $5.4\times10^{-5}$) located at position 98.91 in the internal genetic map.

TABLE 3

Chromosome 5 Markers Significantly Associated with MRCV Resistance at p ≤0.001 in the Argentinian Germplasm

| Marker Name | Relative map position (cM) on PHB map | p-Value | Primers | Reference Sequence |
|---|---|---|---|---|
| PHM15741 | 96.65 | 5.7E−03 | SEQ ID NOs: 17-20 | SEQ ID NO: 45 |
| PHM12093 | 96.91 | 9.4E−05 | SEQ ID NOs: 21-24 | SEQ ID NO:46 |
| PHM15051 | 100.35 | 2.2E−04 | SEQ ID NOs: 25-28 | SEQ ID NO: 47 |
| PHM8091 | 102.58 | 1.8E−04 | SEQ ID NOs: 29-32 | SEQ ID NO: 48 |
| PHM6248 | 102.38 | 5.4E−04 | SEQ ID NOs: 33-36 | SEQ ID NO: 49 |
| PHM9452 | 104.29 | 3.7E−04 | SEQ ID NOs: 37-40 | SEQ ID NO: 50 |

The association studies described in Examples 2 and 3 identified markers associated with MRCV resistance, thereby identifying chromosomal intervals that house QTL associated with MRCV resistance. The identified markers and other markers within the chromosomal intervals that are linked to and associated with the identified markers are useful for identifying and selecting plants that have enhanced resistance to MRCV infection.

Example 4

Validation of the Chromosome 4 and Chromosome 5 QTL in the Biparental Population PHFHH×PHBNB A population of 186 doubled haploids was generated by a cross between PHBNB and PHFHH. Line PHBNB carries favorable haplotypes at both chromosomal intervals and has enhanced resistance to MRCV infection compared to line PHFHH, which carries unfavorable haplotypes at both loci. The doubled haploid lines generated from the cross were phenotyped under natural MRCV infection in the 2007-08 growing season with the reaction to MRCV infection evaluated as described in Example 1. The population was genotyped with a fixed set of 768 SNP markers, and proprietary QTL mapping software was used to analyze the data.

Two of the QTL mapped in the PHBNB×PHFHH population corresponded in position and resistant-parent origin to the intervals encompassing the marker trait associations described in Examples 2 and 3. Chromosome scans are shown in FIGS. 4 and 5. The QTL in chromosome 4 mapped to position 113-132 cM of the PHB map with a peak at position 124 (LRT 7/1). The QTL region in chromosome 5 extended from 78-126 cM of the PHB map with peaks at 82, 97, 104, and 116 (LRTs 8.69, 7.39, 8.0, and 8.63 respectively). The appearance of spurious peaks in the chromosome 5 region could be due to the lack of polymorphic marker coverage.

Example 5

Validation of the Chromosome 5 QTL in the Biparental Population PHFNH×PHKV1

A population of approximately 200 F3 families was developed from a cross between inbreds PHFNH and PHKV1. The population was genotyped with 110 markers and characterized for its reaction to MRCV by growing two replications at a location of natural infection during the 2007-08 growing season. MRCV scores were taken as described in Example I.

The population was grown again during the 2008-09 growing season but MRCV characterization was not possible due to inadequate disease pressure.

QTL analysis revealed a significant QTL on chromosome 5 spanning the 72-121 CM region of the PHB map and peaking at position 89 cM (LRT 8.32). This QTL corresponds to the QTL interval encompassing the chromosome 5 marker trait associations described in Examples 2 and 3. FIG. 6 shows results obtained using proprietary QTL mapping software for chromosome 5.

Example 5

Identification of Markers for Use in Marker Assisted Selection of Plants with Enhanced Resistance to MRCV Infection Closely linked markers that have alleles in linkage disequilibrium with a resistance allele at the QTL on chromosome 4 and/or on chromosome 5 may be effectively used to select for progeny plants with enhanced resistance to MRCV infection. The markers described herein, as well as other markers genetically or physically mapped to the same chromosomal segment, may be used to select for maize plants with enhanced resistance to MRCV infection.

Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. The most proximal polymorphic markers to the gene or locus are used to select for the gene or locus, and the more distal polymorphic markers are used to select against the gene or locus. In an introgression program, this allows for selection of the gene or locus genotype at the more proximal polymorphic markers and selection for the recurrent parent genotype at the more distal polymorphic markers.

Not all markers genetically and physically mapped to the same chromosomal segment as an identified QTL may be used to select for maize plants with enhanced resistance to MRCV infection because the marker may not be informative enough within a particular population.

What is claimed is:

1. A method of obtaining a maize plant with enhanced resistance to Mal de Rio Cuarto Virus ("MRCV") infection, said method comprising:
   a. isolating nucleic acids from a maize plant;
   b. analyzing the isolated nucleic acids for the presence of a QTL allele associated with the enhanced resistance to MRCV, wherein the presence of said QTL allele is determined by detecting a haplotype within an interval on chromosome 4 comprising and flanked by PHM669 and PHM8008, wherein the reference sequence for PHM669 is SEQ ID NO:42 and the reference sequence for PHM8008 is SEQ ID NO:44, and said haplotype comprises: an "A" at position 85, a "C" at position 344, and an "A" at position 355 relative to SEQ ID NO:42;
   c. selecting a maize plant having said QTL allele, based on the analysis of step b;
   d. crossing said maize plant to a second maize plant;
   e. evaluating progeny from said cross for the QTL allele; and
   f. selecting progeny plants that possess the QTL allele.

* * * * *

SEQUENCE LISTING

```
<160> NUMBER OF SEQ ID NOS: 75

<210> SEQ ID NO 1
<211> LENGTH: 19
<212> TYPE: DNA
<213> ORGANISM: Artificial
<220> FEATURE:
<223> OTHER INFORMATION: PHM1718 external forward primer

<400> SEQUENCE: 1
cgcacgagtt cgaggtgaa                                              19

<210> SEQ ID NO 2
<211> LENGTH: 18
<212> TYPE: DNA
<213> ORGANISM: Artificial
<220> FEATURE:
<223> OTHER INFORMATION: PHM1718 internal forward primer

<400> SEQUENCE: 2
agcgccggga cctggaga                                               18

<210> SEQ ID NO 3
<211> LENGTH: 21
<212> TYPE: DNA
<213> ORGANISM: Artificial
<220> FEATURE:
<223> OTHER INFORMATION: PHM1718 internal reverse primer

<400> SEQUENCE: 3
gaactacaga ccaaaccaag c                                           21

<210> SEQ ID NO 4
<211> LENGTH: 21
<212> TYPE: DNA
<213> ORGANISM: Artificial
<220> FEATURE:
<223> OTHER INFORMATION: PHM1718 external reverse primer

<400> SEQUENCE: 4
gaacacaaac gattgagcac g                                           21
```

```
<210> SEQ ID NO 5
<211> LENGTH: 19
<212> TYPE: DNA
<213> ORGANISM: Artificial
<220> FEATURE:
<223> OTHER INFORMATION: PHM669 external forward primer

<400> SEQUENCE: 5
tcatcttcac ctgggtcga                                                  19

<210> SEQ ID NO 6
<211> LENGTH: 20
<212> TYPE: DNA
<213> ORGANISM: Artificial
<220> FEATURE:
<223> OTHER INFORMATION: PHM669 internal forward primer

<400> SEQUENCE: 6
gtcgttggct ttgtggaact                                                 20

<210> SEQ ID NO 7
<211> LENGTH: 22
<212> TYPE: DNA
<213> ORGANISM: Artificial
<220> FEATURE:
<223> OTHER INFORMATION: PHM669 internal reverse primer

<400> SEQUENCE: 7
agggaaaaaa caaaaagaat gt                                              22

<210> SEQ ID NO 8
<211> LENGTH: 21
<212> TYPE: DNA
<213> ORGANISM: Artificial
<220> FEATURE:
<223> OTHER INFORMATION: PHM669 external reverse primer

<400> SEQUENCE: 8
gaaagacctt acattcatgc a                                               21

<210> SEQ ID NO 9
<211> LENGTH: 21
<212> TYPE: DNA
<213> ORGANISM: Artificial
<220> FEATURE:
<223> OTHER INFORMATION: PHM11786 external forward primer

<400> SEQUENCE: 9
cagagctttc ttcagacttg t                                               21

<210> SEQ ID NO 10
<211> LENGTH: 22
<212> TYPE: DNA
<213> ORGANISM: Artificial
<220> FEATURE:
<223> OTHER INFORMATION: PHM11786 internal forward primer

<400> SEQUENCE: 10
ggaataagtt ttcggattac aa                                              22

<210> SEQ ID NO 11
<211> LENGTH: 22
<212> TYPE: DNA
<213> ORGANISM: Artificial
<220> FEATURE:
<223> OTHER INFORMATION: PHM11786 internal reverse primer
```

```
<400> SEQUENCE: 11
ttatatttgt gcaggctgaa tc                                              22

<210> SEQ ID NO 12
<211> LENGTH: 22
<212> TYPE: DNA
<213> ORGANISM: Artificial
<220> FEATURE:
<223> OTHER INFORMATION: PHM11786 external reverse primer

<400> SEQUENCE: 12
tgccaaattg caacatggtt ta                                              22

<210> SEQ ID NO 13
<211> LENGTH: 21
<212> TYPE: DNA
<213> ORGANISM: Artificial
<220> FEATURE:
<223> OTHER INFORMATION: PHM8008 external forward primer

<400> SEQUENCE: 13
tcctgggttg tgccttctta t                                               21

<210> SEQ ID NO 14
<211> LENGTH: 18
<212> TYPE: DNA
<213> ORGANISM: Artificial
<220> FEATURE:
<223> OTHER INFORMATION: PHM8008 internal forward primer

<400> SEQUENCE: 14
atgctgttaa agattcct                                                   18

<210> SEQ ID NO 15
<211> LENGTH: 20
<212> TYPE: DNA
<213> ORGANISM: Artificial
<220> FEATURE:
<223> OTHER INFORMATION: PHM8008 internal reverse primer

<400> SEQUENCE: 15
tctcttcatg cccagtgcta                                                 20

<210> SEQ ID NO 16
<211> LENGTH: 21
<212> TYPE: DNA
<213> ORGANISM: Artificial
<220> FEATURE:
<223> OTHER INFORMATION: PHM8008 external reverse primer

<400> SEQUENCE: 16
tttgtccaca ggtttctgag c                                               21

<210> SEQ ID NO 17
<211> LENGTH: 21
<212> TYPE: DNA
<213> ORGANISM: Artificial
<220> FEATURE:
<223> OTHER INFORMATION: PHM15741 external forward primer

<400> SEQUENCE: 17
tcttcagttc cttgagagga g                                               21

<210> SEQ ID NO 18
<211> LENGTH: 20
```

```
<212> TYPE: DNA
<213> ORGANISM: Artificial
<220> FEATURE:
<223> OTHER INFORMATION: PHM15741 internal forward primer

<400> SEQUENCE: 18
tcatgttcct gctgctgtca                                              20

<210> SEQ ID NO 19
<211> LENGTH: 20
<212> TYPE: DNA
<213> ORGANISM: Artificial
<220> FEATURE:
<223> OTHER INFORMATION: PHM15741 internal reverse primer

<400> SEQUENCE: 19
atgcataagg ccctattcgg                                              20

<210> SEQ ID NO 20
<211> LENGTH: 22
<212> TYPE: DNA
<213> ORGANISM: Artificial
<220> FEATURE:
<223> OTHER INFORMATION: PHM15741 external reverse primer

<400> SEQUENCE: 20
cgcttaaaca tccaattatt gc                                           22

<210> SEQ ID NO 21
<211> LENGTH: 22
<212> TYPE: DNA
<213> ORGANISM: Artificial
<220> FEATURE:
<223> OTHER INFORMATION: PHM12093 external forward primer

<400> SEQUENCE: 21
tcaagattcg acctatatcc at                                           22

<210> SEQ ID NO 22
<211> LENGTH: 22
<212> TYPE: DNA
<213> ORGANISM: Artificial
<220> FEATURE:
<223> OTHER INFORMATION: PHM12093 internal forward primer

<400> SEQUENCE: 22
atatatcaag ggcatgttta gt                                           22

<210> SEQ ID NO 23
<211> LENGTH: 19
<212> TYPE: DNA
<213> ORGANISM: Artificial
<220> FEATURE:
<223> OTHER INFORMATION: PHM12093 internal reverse primer

<400> SEQUENCE: 23
tgacgtcttg tggtgtctc                                               19

<210> SEQ ID NO 24
<211> LENGTH: 19
<212> TYPE: DNA
<213> ORGANISM: Artificial
<220> FEATURE:
<223> OTHER INFORMATION: PHM12093 external reverse primer

<400> SEQUENCE: 24
```
cgtgctggaa tgatgagta                                                19

<210> SEQ ID NO 25
<211> LENGTH: 20
<212> TYPE: DNA
<213> ORGANISM: Artificial
<220> FEATURE:
<223> OTHER INFORMATION: PHM15051 external forward primer

<400> SEQUENCE: 25
agcaggttcg ggactatgtt                                               20

<210> SEQ ID NO 26
<211> LENGTH: 18
<212> TYPE: DNA
<213> ORGANISM: Artificial
<220> FEATURE:
<223> OTHER INFORMATION: PHM15051 internal forward primer

<400> SEQUENCE: 26
gttccatcca gatctagt                                                 18

<210> SEQ ID NO 27
<211> LENGTH: 21
<212> TYPE: DNA
<213> ORGANISM: Artificial
<220> FEATURE:
<223> OTHER INFORMATION: PHM15051 internal reverse primer

<400> SEQUENCE: 27
gccgcgagat tcaaatgtca t                                             21

<210> SEQ ID NO 28
<211> LENGTH: 20
<212> TYPE: DNA
<213> ORGANISM: Artificial
<220> FEATURE:
<223> OTHER INFORMATION: PHM15051 external reverse primer

<400> SEQUENCE: 28
gcacccgaat ctgctgaaat                                               20

<210> SEQ ID NO 29
<211> LENGTH: 20
<212> TYPE: DNA
<213> ORGANISM: Artificial
<220> FEATURE:
<223> OTHER INFORMATION: PHM8091 external forward primer

<400> SEQUENCE: 29
aggatcttcc tcgaggagac                                               20

<210> SEQ ID NO 30
<211> LENGTH: 19
<212> TYPE: DNA
<213> ORGANISM: Artificial
<220> FEATURE:
<223> OTHER INFORMATION: PHM8091 internal forward primer

<400> SEQUENCE: 30
acgacatcca ggagcgcat                                                19

<210> SEQ ID NO 31
<211> LENGTH: 20
<212> TYPE: DNA
<213> ORGANISM: Artificial

```
<220> FEATURE:
<223> OTHER INFORMATION: PHM8091 internal reverse primer

<400> SEQUENCE: 31
gccaatcatc ttgccaagag                                                20

<210> SEQ ID NO 32
<211> LENGTH: 22
<212> TYPE: DNA
<213> ORGANISM: Artificial
<220> FEATURE:
<223> OTHER INFORMATION: PHM8091 external reverse primer

<400> SEQUENCE: 32
gtgaatccat ctttgcaaat cg                                             22

<210> SEQ ID NO 33
<211> LENGTH: 21
<212> TYPE: DNA
<213> ORGANISM: Artificial
<220> FEATURE:
<223> OTHER INFORMATION: PHM6248 external forward primer

<400> SEQUENCE: 33
ccctttgttt gaatagtcta t                                              21

<210> SEQ ID NO 34
<211> LENGTH: 18
<212> TYPE: DNA
<213> ORGANISM: Artificial
<220> FEATURE:
<223> OTHER INFORMATION: PHM6248 internal forward primer

<400> SEQUENCE: 34
cgattttgta cactagaa                                                  18

<210> SEQ ID NO 35
<211> LENGTH: 18
<212> TYPE: DNA
<213> ORGANISM: Artificial
<220> FEATURE:
<223> OTHER INFORMATION: PHM6248 internal reverse primer

<400> SEQUENCE: 35
gtgtttgtta tgcgagat                                                  18

<210> SEQ ID NO 36
<211> LENGTH: 18
<212> TYPE: DNA
<213> ORGANISM: Artificial
<220> FEATURE:
<223> OTHER INFORMATION: PHM6248 external reverse primer

<400> SEQUENCE: 36
tgcaagcgaa ggcagcta                                                  18

<210> SEQ ID NO 37
<211> LENGTH: 20
<212> TYPE: DNA
<213> ORGANISM: Artificial
<220> FEATURE:
<223> OTHER INFORMATION: PHM9452 external forward primer

<400> SEQUENCE: 37
acgtggagtt ggtgatcgta                                                20
```

<210> SEQ ID NO 38
<211> LENGTH: 19
<212> TYPE: DNA
<213> ORGANISM: Artificial
<220> FEATURE:
<223> OTHER INFORMATION: PHM9452 internal forward primer

<400> SEQUENCE: 38
tggttcctcc ttcggcggt                                              19

<210> SEQ ID NO 39
<211> LENGTH: 22
<212> TYPE: DNA
<213> ORGANISM: Artificial
<220> FEATURE:
<223> OTHER INFORMATION: PHM9452 internal reverse primer

<400> SEQUENCE: 39
tatgatgtga tgatgaggac tc                                          22

<210> SEQ ID NO 40
<211> LENGTH: 20
<212> TYPE: DNA
<213> ORGANISM: Artificial
<220> FEATURE:
<223> OTHER INFORMATION: PHM9452 external reverse primer

<400> SEQUENCE: 40
atgcatcgcg ggtgtcttta                                             20

<210> SEQ ID NO 41
<211> LENGTH: 514
<212> TYPE: DNA
<213> ORGANISM: Artificial
<220> FEATURE:
<223> OTHER INFORMATION: PHM1718 reference sequence

<400> SEQUENCE: 41
tcccgggact ggagaggtgt gcagactacg gcaagacatc cacttctggc aggtggacgc    60
ggcgacgcgc tcccgctcgg cctcccgcag atcatgatgg tgctcacccg cgagggccag   120
cttcggcagg acctcgctga ctgtacggcg tgctcgcaga ttgagtatct gtgatctctc   180
tctgatctct cttttttttac tgatggattt gaacctgcaa tgtacgtgca ggtgtggaga   240
agaagttcgg tgtctccttc cagaaggaga gggagaaccg ggcgtacatg agcggaccgg   300
agcatggtat ccacccgcta gcgaacgcta ccggcaaggg cctgaggacc gagatccgtg   360
aggtcgattt gccggcgagt actaccgccg gcgccgggag ggtcttcact tgatcgccgt   420
atcgtgtgtt gccgcggcgg gtctgcgtaa tgtagactat atagactgtg cttggtttgg   480
tctgtagttc atggtcatag ctttccttcc gggg                              514

<210> SEQ ID NO 42
<211> LENGTH: 473
<212> TYPE: DNA
<213> ORGANISM: Artificial
<220> FEATURE:
<223> OTHER INFORMATION: PHM669 reference sequence

<400> SEQUENCE: 42
attatcccct atcaccccctt cgttggcttt gtggactgag catgttcatg gttgggatgt    60
cacgcccaca cggttccagc tcacgacctc tgatgagcag caggcgacat ccgaatatta   120
tctgcatcta catgaacaag ggggctggaa gctttaccat gttggtgatt tgtcatatc   180

```
aaattccgat gagcccatga aactcaagtt ctcaatgatg cagatcgatt gcacacatat    240
gaaaggcggc ttgtgcgttg actccgtgtt tatatatcct aaagggtaca agcctgagaa    300
ggcgaacata gtctgcacct agttcggcaa agttggcctt gtacctctcc tgcatgatga    360
aacaagaggc aattcaaatg tggatggcta gccttttttcc tggcgatcct tacctgaaag    420
cccattgtac attctttttg tttttttccct atggtcatag ctgccttccc ccc           473
```

<210> SEQ ID NO 43
<211> LENGTH: 479
<212> TYPE: DNA
<213> ORGANISM: Artificial
<220> FEATURE:
<223> OTHER INFORMATION: PHM11786 reference sequence

<400> SEQUENCE: 43

```
atctgattcg gggaaggtcc cagtcacaac gggaataagt tttcggatta caaatgtgaa     60
atatcatacc tccttttatt cagtcttact attcattctg ttagcaccat tggtctatgg    120
gtgcacaaac taatctaata ttcatgagga ataaattagc aacagtaaat tgatatatac    180
cacatgatta aaggcatcca ttctaagtaa tcaaattagg gatcatgcaa ctgaatctta    240
ggaacatatg aatgacacac acaaaaatta caagttcaac aattttgcat tattgaagtg    300
gcataaaaat caatggttag ttgcttattt atgtatatgc ttctgaacaa atagcaagag    360
cacagggatt gctatcaaca caaaccttag catcagaagt acttgcaact ggagcatctg    420
gaaccttctg cttcaacgat tgtttcatga ttcagcctca ctgtttactt tcgggataa    479
```

<210> SEQ ID NO 44
<211> LENGTH: 736
<212> TYPE: DNA
<213> ORGANISM: Artificial
<220> FEATURE:
<223> OTHER INFORMATION: PHM8008 reference sequence

<400> SEQUENCE: 44

```
aaaaatttag gccttggaaa ataagatcaa aaaaattccc cggtggttaa caggttgctg     60
gttactggac cttttaactt tctgaatttt ctgtttgggg ctatttaacc ccaatggtgc    120
cctgtgcaat aaatgaacgc cagaagaaaa aagtcccgtc ttgcatcatc gcaatatatt    180
atgttgatgc gtcgaatgca tatacctaca tcatattacc aaacccgcct tgatttgatt    240
cagaattcgg tcgtgtgaac ttgatatctc atcatgaatc aaaagtatta tggatgaaat    300
tatgtgcaca ccttttggcca tatgtggcag actcattaaa atgaccattt cccatacttg    360
tggttatgca cgttttgcca gagtcttgcg cagtatcttg atgccgtttc accaccatag    420
tgttcttgac atgccttgtt tgtggttgcc cttctcaggt ctcctaatta catacgttgc    480
cttgaacctt atggatggcc atggccagcc ggctctcctt tacatcgtgc ctttcacaat    540
cggtaagtga tgcctgcccc tgacgatagt atctatctat gtatgtagga gtatttcatg    600
ccatgtcttc tggataggtt cctgtttttt tgttttgttc tattgttttg tttgttttaa    660
cgaaatacca aatttgtgca ggcaccttct tagcactggc atgaaacttt ctagtagtgg    720
gtaaaagggg cgttta                                                   736
```

<210> SEQ ID NO 45
<211> LENGTH: 654
<212> TYPE: DNA
<213> ORGANISM: Artificial
<220> FEATURE:

<223> OTHER INFORMATION: PHM15741 reference sequence

<400> SEQUENCE: 45

| cccggcccaa | ttttaaacc | ccgcgactt | tttaaacccc | ctgctgtcag | cgcagcagca | 60 |
| gcaggtggcg | ggcctgtcca | agttctgccg | ctgctaccgg | aactgctaca | ccgactgcag | 120 |
| gaagtccacg | ggccgctacc | cctgcaacgc | caactgcttt | caggactgca | tcaacgggat | 180 |
| gctgccgccg | gctccggcgg | aggtcgtcgt | ccccgccgac | tgccgcgaca | tctgcctcat | 240 |
| gggcttctgc | ggctccatgg | agatcgccgg | tgacggtgag | gccagctagc | tagctaactt | 300 |
| ctggacaata | atctgataga | caggcatata | tgcatgcatg | catacttcag | ttcgatagta | 360 |
| taacctttcg | atcatagatg | aatgaaatct | gactgcttcc | tgtgaattaa | tgttgtattt | 420 |
| cagccgtggc | tggggatgcc | gaggcgtgtg | tggctgactg | caccaagaac | ctcggtgcct | 480 |
| ttgcaccaag | tgcagccaag | acgatcaact | gaagcatgca | ttagggcccg | ttcgcttgta | 540 |
| caggattaaa | ccggaattcg | ttccagctca | tcaaaatcta | tataaattaa | agaagtaatc | 600 |
| cggttaggaa | ttaattcgaa | gctccaatcc | ctaaaaaccg | attagggccy | tatg | 654 |

<210> SEQ ID NO 46
<211> LENGTH: 515
<212> TYPE: DNA
<213> ORGANISM: Artificial
<220> FEATURE:
<223> OTHER INFORMATION: PHM12093 reference sequence

<400> SEQUENCE: 46

| tagcctttcc | ccagttttaa | gggcatgttt | agttctcgac | taactgtact | aggcttagag | 60 |
| gtgaggtgtt | tagttctcga | ctaactaact | gtctagaggt | gaggtaatgg | gctctaattt | 120 |
| tatattatta | taaaatggaa | gaatcgaatc | aaatttgaac | cttagtcaaa | ctaaaattaa | 180 |
| ttaaagttcc | taactcatta | tgaagaagca | tttagatcgt | gattcattac | cactactaat | 240 |
| tatgcataac | ttgtctaagg | ttagtcgacc | aaattaaaga | actaacctta | gataaaaaca | 300 |
| aattaggaac | cagattaggc | aggtcgtaaa | tctctctact | accatcatat | gccgaaaatg | 360 |
| attaggacga | agagacggtt | taggcagttc | gtaaccgtac | atactcatct | ccggaagtgc | 420 |
| atagcatcag | tacacagaca | gtcccagtca | tccgaagacg | actttagaac | gtggagacac | 480 |
| cacaagacgt | caatggtcat | agctgcccctt | ccccc | | | 515 |

<210> SEQ ID NO 47
<211> LENGTH: 671
<212> TYPE: DNA
<213> ORGANISM: Artificial
<220> FEATURE:
<223> OTHER INFORMATION: PHM15051 reference sequence

<400> SEQUENCE: 47

| gcgagagccc | ccttaccaga | ctagtaccag | atctagtagg | ctcacgggca | cgacagatga | 60 |
| agtaagacaa | gttgcacgtg | cttatcgagt | ttactatatg | aagacagagg | aggagggttc | 120 |
| tgactacctt | gttgatcact | caattgtcat | gtatgctatt | tctaatctcc | atcttgcaca | 180 |
| atggctttag | gcatttagct | aattgtgatt | ctgatgatac | tctgcaattg | ggatggtcta | 240 |
| gctcatgtca | tttcattatt | gcacgatacg | ccatacctac | agcatgcaaa | ccaaaacgaa | 300 |
| gaaaccagct | aatttggctc | ttgtttttt | taagattctg | aatattatct | tgggagactc | 360 |
| aaatgggtat | ctagtaggat | ttgttatggt | attggatact | gtgaagactc | agaatgttaa | 420 |
| ctctagccta | ccccaacttg | cttgggataa | aaggctgtgt | tgttttttgtt | gtattggata | 480 |

```
ctgtgaaaac tcaggatatc aaatacaggg aatgtctcga tcccgatacc acatgctggc    540
tgcagttgtg ttctccttgc actcactgca gctatagaaa acattgattt gttgatgcaa    600
ctgctatgtt tttatcatta tgatagctat taagattctt tatgttgttt caaaacactg    660
actgactggt t                                                         671

<210> SEQ ID NO 48
<211> LENGTH: 588
<212> TYPE: DNA
<213> ORGANISM: Artificial
<220> FEATURE:
<223> OTHER INFORMATION: PHM8091 reference sequence

<400> SEQUENCE: 48
ccagtcataa tgacgatatc caggagcgca tggccgcgcg cctcaggcac ctgggtatac     60
gcgtccgaag cgtcgaggag gacgagcgct gcgtcatccc catgggaggg ccgctgcccg    120
tcctgccgca gagggttgtc ggcatcggcg gcacggcagg gatggtgcac ccgtccacgg    180
gctacatggt ggcgcgcacg cttgccaccg cgcctatcgt ggcggacgcc atcgtaaggt    240
tcctcgacac cggcaccggc aacggcatgg gtggcctggc aggggacgcg ctctccgccg    300
aggtgtggaa gcagctgtgg ccagccaaca ggcggcggca gagggagttc ttctgcttcg    360
gcatggacgt cctgctcaag ctggacctcg agggaacgcg gcggttcttc gacgccttct    420
tcgacctgga gccacactac tggcacggtt cctgtcatc cagactgttc ctgccggagc     480
tcttgatgtt cggcctcgca ctgttcggga acgcctccaa ctcgtcgagg ctggagatca    540
tggccaaggc accgtgcctc ttgcaagttg ttacttttcg tataattt                 588

<210> SEQ ID NO 49
<211> LENGTH: 504
<212> TYPE: DNA
<213> ORGANISM: Artificial
<220> FEATURE:
<223> OTHER INFORMATION: PHM6248 reference sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t

<400> SEQUENCE: 49 cnmnnnccc gaattttgtc cagaaatatt ttcttaaatt tgtactagaa ttattttctt      60
aaaattccta cttttaagtg tatgaatttc atatttaaaa gcatcattag cataataaat    120
aagtaaatca ataaaacaat ggaattgcct tcatgccaag atttatttga atgattgcat    180
attgtctgga atccagatta aagtaaaatt tgaatcaagt ttgaatttgt agtttgaaat    240
aaaacataaa atagaaaagg gaaacaaaaa agggaaaacc tcacctgggc catgtaccac    300
tcacttggcc ccactgcctt acttgtgtca gcccaacacc ggcccgtcag cctctccaca    360
ccgcgcgcta gtgttgcctt aagtcaccgg tggttgggc ccaccttcg ggtccctccc      420 cttcgtcatc tccgaaccgg tgtgagcacc aaaaactcca tggatctcgc ataacaaaca    480
catggtcata gcctgttacc cacc                                           504

<210> SEQ ID NO 50
<211> LENGTH: 630
<212> TYPE: DNA
```

```
<213> ORGANISM: Artificial
<220> FEATURE:
<223> OTHER INFORMATION: PHM9452 reference sequence

<400> SEQUENCE: 50
atttccgccc tggtgactgg tactgctcct gcggcgaaaa caacttcgcc agccgctcca        60
actgcttcag gtgctctgcc tacaaggagg aggctgccgg cgcctttgat agtgacatgt       120
cacgctcacg cggctacgcc ggcttcggca gcggcgctgc cgcccgtacc aaccgccccg       180
gttggaagtc tggagactgg atctgcacca ggtgctgcgt cgtgttttaa tttgtggctt       240
ttctttctgt ctgcatgcat atgtgcatgg aatgatgagg ttgctgaata atatatatat       300
tttacgtaca caggtccggt tgcaacgagc acaacttcgc tagcaggatg gaatgtttca       360
ggtgcaacgc gccacgggac tccggtagcg ctgccacgac gacctacgaa aactacttgt       420
aatttaccaa ataaatccat atatttcctc ctttaatttt gctggctgct gtgtgtgcat       480
gcatgatctg accgaacgtt ccgtttgctg caggcactga ggtgtaggta gagcaaagtt       540
tacagctata gcgcgcgtcg acgaagcagg agcagcagca gcagcatgaa ttgaagagag       600
tcctcatcat cactttaact ttccttataa                                        630

<210> SEQ ID NO 51
<211> LENGTH: 20
<212> TYPE: DNA
<213> ORGANISM: artificial
<220> FEATURE:
<223> OTHER INFORMATION: PHM12615 external forward primer

<400> SEQUENCE: 51
atgccatgat gtacgggact                                                    20

<210> SEQ ID NO 52
<211> LENGTH: 19
<212> TYPE: DNA
<213> ORGANISM: artificial
<220> FEATURE:
<223> OTHER INFORMATION: PHM12615 internal forward primer

<400> SEQUENCE: 52
tagttcatgc tgttggtgg                                                     19

<210> SEQ ID NO 53
<211> LENGTH: 20
<212> TYPE: DNA
<213> ORGANISM: artificial
<220> FEATURE:
<223> OTHER INFORMATION: PHM12615 internal reverse primer

<400> SEQUENCE: 53
cgtcctgcaa aattcaggac                                                    20

<210> SEQ ID NO 54
<211> LENGTH: 20
<212> TYPE: DNA
<213> ORGANISM: artificial
<220> FEATURE:
<223> OTHER INFORMATION: PHM12615 external reverse primer

<400> SEQUENCE: 54
tttggctgtt gcgacgcaca                                                    20

<210> SEQ ID NO 55
<211> LENGTH: 21
```

```
<212> TYPE: DNA
<213> ORGANISM: artificial
<220> FEATURE:
<223> OTHER INFORMATION: PHM5713 external forward primer

<400> SEQUENCE: 55
ctacgactac ttccatgaca a                                              21

<210> SEQ ID NO 56
<211> LENGTH: 21
<212> TYPE: DNA
<213> ORGANISM: artificial
<220> FEATURE:
<223> OTHER INFORMATION: PHM5713 internal forward primer

<400> SEQUENCE: 56
cattgccact gtgctgatgt a                                              21

<210> SEQ ID NO 57
<211> LENGTH: 20
<212> TYPE: DNA
<213> ORGANISM: artificial
<220> FEATURE:
<223> OTHER INFORMATION: PHM5713 internal reverse primer

<400> SEQUENCE: 57
ttccggcaga agccaggtgc                                                20

<210> SEQ ID NO 58
<211> LENGTH: 20
<212> TYPE: DNA
<213> ORGANISM: artificial
<220> FEATURE:
<223> OTHER INFORMATION: PHM5713 external reverse primer

<400> SEQUENCE: 58
aggaccgata ccttactctg                                                20

<210> SEQ ID NO 59
<211> LENGTH: 22
<212> TYPE: DNA
<213> ORGANISM: artificial
<220> FEATURE:
<223> OTHER INFORMATION: PHM6921 external forward primer

<400> SEQUENCE: 59
ctagcaaaca atcagctctt tg                                             22

<210> SEQ ID NO 60
<211> LENGTH: 22
<212> TYPE: DNA
<213> ORGANISM: artificial
<220> FEATURE:
<223> OTHER INFORMATION: PHM6921 internal forward primer

<400> SEQUENCE: 60
atcaagaatg gtacaacatt gg                                             22

<210> SEQ ID NO 61
<211> LENGTH: 21
<212> TYPE: DNA
<213> ORGANISM: artificial
<220> FEATURE:
<223> OTHER INFORMATION: PHM6921 internal reverse primer

<400> SEQUENCE: 61
```

```
agtcataggg agcgatttat c                                       21

<210> SEQ ID NO 62
<211> LENGTH: 21
<212> TYPE: DNA
<213> ORGANISM: artificial
<220> FEATURE:
<223> OTHER INFORMATION: PHM6921 external reverse primer

<400> SEQUENCE: 62
cttctcagat gaaatgacgc t                                       21

<210> SEQ ID NO 63
<211> LENGTH: 21
<212> TYPE: DNA
<213> ORGANISM: artificial
<220> FEATURE:
<223> OTHER INFORMATION: PHM1683 external forward primer

<400> SEQUENCE: 63
tttgcataca aacttccctg g                                       21

<210> SEQ ID NO 64
<211> LENGTH: 22
<212> TYPE: DNA
<213> ORGANISM: artificial
<220> FEATURE:
<223> OTHER INFORMATION: PHM1683 internal forward primer

<400> SEQUENCE: 64
taatgcctca aaaaattgca ta                                      22

<210> SEQ ID NO 65
<211> LENGTH: 21
<212> TYPE: DNA
<213> ORGANISM: artificial
<220> FEATURE:
<223> OTHER INFORMATION: PHM1683 internal reverse primer

<400> SEQUENCE: 65
tcctttctgc aggttaacca t                                       21

<210> SEQ ID NO 66
<211> LENGTH: 20
<212> TYPE: DNA
<213> ORGANISM: artificial
<220> FEATURE:
<223> OTHER INFORMATION: PHM1683 external reverse primer

<400> SEQUENCE: 66
cgaaattgct gctgctgaag                                         20

<210> SEQ ID NO 67
<211> LENGTH: 18
<212> TYPE: DNA
<213> ORGANISM: artificial
<220> FEATURE:
<223> OTHER INFORMATION: PHM17281 external forward primer

<400> SEQUENCE: 67
acacgacacg aaccctcg                                           18

<210> SEQ ID NO 68
<211> LENGTH: 18
<212> TYPE: DNA
<213> ORGANISM: artificial
```

```
<220> FEATURE:
<223> OTHER INFORMATION: PHM17281 internal forward primer

<400> SEQUENCE: 68
cctcatcgac gtccagaa                                                  18

<210> SEQ ID NO 69
<211> LENGTH: 19
<212> TYPE: DNA
<213> ORGANISM: artificial
<220> FEATURE:
<223> OTHER INFORMATION: PHM17281 internal reverse primer

<400> SEQUENCE: 69
acatggcgtc atccagggt                                                 19

<210> SEQ ID NO 70
<211> LENGTH: 20
<212> TYPE: DNA
<213> ORGANISM: artificial
<220> FEATURE:
<223> OTHER INFORMATION: PHM17281 external reverse primer

<400> SEQUENCE: 70
cctggttccc tagttcttac                                                20

<210> SEQ ID NO 71
<211> LENGTH: 441
<212> TYPE: DNA
<213> ORGANISM: artificial
<220> FEATURE:
<223> OTHER INFORMATION: PHM12615 reference sequence

<400> SEQUENCE: 71
gaaaaaggga aggtcccagt caaaacgtag ttcatgctgt tggtggtctc cgcgacacag     60
tccaacatta taatccctac gaggaggttg gagttggatg acttttgag aaagcagagg    120 caaacagaat gatcgatgcc ctagggcact gcttgaacac atacagaaat tactggagca   180
gttgggaagg tatccaacgt agagggatga tgcaggacct aagctgggat aacgctgcta   240
aactctacga ggaagttctt cttgccgcca aatatcagtg gtgactgttg ttgaactgtc   300
caaggaactg ttgatatttg tcattcatag acctgaaggc tttctgtcgc atagaagtca   360
ccgactgttt caattctttt ggtgactgct tcacacagct gctgcatgct ttgtcccgaa   420
tttgcagaac ttttcttgtt a                                             441

<210> SEQ ID NO 72
<211> LENGTH: 718
<212> TYPE: DNA
<213> ORGANISM: artificial
<220> FEATURE:
<223> OTHER INFORMATION: PHM5713 reference sequence

<400> SEQUENCE: 72
gggagccccc catttcactg tgctgatgtc ctatcaaatg tcgagaaggg tggagagacc     60
atcttcccca atgcagaggt agtgtacttg tccttcctgt gtttaccccc ttaagaatgc    120
cagttgtaat gacttgaaca ttccataggg gaagctattg caacccaagg acgacacttg    180
gtctgattgt gcaagaaacg gatatgcagg tatagcaatt gttctggta gaactctagt    240 tacatcgcag atctgcactc tatatcacct ggcttgacca gttcttacat aatgtgacta    300
tggcccatgg ctccttttgc ttgataatgt cactagagtc tagtttctca gcaggctttc   360
```

| | |
|---|---|
| ttaccttggt acttgcacat cacgcgagta ccttactcca tgcatattca ctcactcgga | 420 |
| tgtctatctg ctgctggttt ccttctgcag ttaaaccggt aaagggtgat gccctgctgt | 480 |
| tcttcagtct ccaccctgat tcaacaacag actctgacag cttgcacggt agctgccccg | 540 |
| tcatcgaagg ccaaaagtgg tccgcgacta aatggatcca tgtgaggtca tttgacctca | 600 |
| ccgtcaagca gccgggtccc tctgatggat tttaggacaa aaatgtcctc tgccccatt | 660 |
| gggcggcctt gggcaattcc ccaaaaacct aattaatggt ggggaccagg aacccctg | 718 |

```
<210> SEQ ID NO 73
<211> LENGTH: 505
<212> TYPE: DNA
<213> ORGANISM: artificial
<220> FEATURE:
<223> OTHER INFORMATION: PHM6921 reference sequence

<400> SEQUENCE: 73
```

| | |
|---|---|
| aaaaacgtgg aagtcccagt cacaacaatc aagaatggta caacattgga atgatcaggt | 60 |
| caaaaaagga gtcacatgtg caaatgaatc gtcattgtcc tcttgactgt gagaggcatt | 120 |
| tggagctgaa atattggtac cacgaccacc ggtggcacca tgaccacttg aggaggaagc | 180 |
| accaataggt cgaggtatac cacgtccatg agaggaggtg ctccatgctg cacaaccact | 240 |
| tctaggaccc tcgctggtcg ttcgtggaac tctgaggcct ctgcctgtaa caccacgacc | 300 |
| aataccagct gatcaagaat gactacgacc cctgtgacca tcatgaactg gagtagcatg | 360 |
| gtagttagca atgaactggg actgacgaag gtcttgaaat gatgtaatgt tctagaactc | 420 |
| cacgtcgctg gagttgaggt ccaacctgtc cattctacca gatcgtgaga agcgataaat | 480 |
| cgtccctaaa actttgactt taacc | 505 |

```
<210> SEQ ID NO 74
<211> LENGTH: 645
<212> TYPE: DNA
<213> ORGANISM: artificial
<220> FEATURE:
<223> OTHER INFORMATION: PHM1683 reference sequence

<400> SEQUENCE: 74
```

| | |
|---|---|
| awttcaaaat tgctaacact agtacaaatg ggaacaagtc aaggtatggc attctacatg | 60 |
| acttattaac actgttgatg gtaccactgg tagtccttga tgtgttattt gccttcagaa | 120 |
| tgccgtttgt ttttttgccat gtagttctaa aattatcatc tttgctttga aatgccttat | 180 |
| gctacaattt ttgcacccct ttttcatctt atttcgttgg cttcatggat tactttcatg | 240 |
| aatcctttat atccttctta aatagtgaat gttaaactta tgacataata ataattaata | 300 |
| aggtgatata ctaggtttta ttttgcatag ttgggctgtt agcataatca cactaatgtt | 360 |
| cttgcactaa gaatgtcagc tttgcctttg ctttttctag agcacttacc ttttaagtag | 420 |
| atatttgtct aatctgtatt atcaacctag caacgcttca agtgccggta tgctatctta | 480 |
| ttgcgtgcca tctgttatat ttttctgttc ttttaacaac cctttggtat tactatatta | 540 |
| ggagatcctc ggtgactgtg gccgagctgc aatccagaca caaggctcca tgaacaatcc | 600 |
| atttggatca acttttgtat atggttatca gaatatcgct ttcga | 645 |

```
<210> SEQ ID NO 75
<211> LENGTH: 681
<212> TYPE: DNA
<213> ORGANISM: artificial
<220> FEATURE:
<223> OTHER INFORMATION: PHM17281 reference sequence
```

```
<400> SEQUENCE: 75
agcctgcyac cgacgtcgtc gacaagctga catcgctcga gaccaagatg acgacggacc        60
acaaaccact acttatcgac gtcagaagct gctcaccgac gtcgtcgaca agctgacatc       120
gctcgagacc aagatgacga cggtcgagcg cgagctctgc accgtcaagc tcgatcaacg       180
gcgcctccac gatgccgtcg aggctgggaa gcaggccgcg ttccccggag tactcgagct       240
gcgtttaccg gagtacgacg gcacggacga ccccgccata tggctccacc gcttcgagct       300
gttcttcagc ctgcagcgga ccgaggacga cgacaaggtg tgcctcgcgg ccttccacat       360
gaccggcgcg gcgcagatct ggtactcctt gctcaagcac aaccgcggcg tccctacctg       420
gccgcagctc gccgagtcgg tgcgtcgccg cttcggcgcc ccgacgagcg ggtacgcgct       480
ccgcgagctc ctccggctgc ggcacactgg ctccgtcgcg gagtaccggg acgagttcct       540
gaggctgctg gacagatgcg acggcgtgac ggagccgctg caggtggcct tctttaccgc       600
cggtctccgc gatccgctgc tcaccgacgt gaagctgcgg caaccggcaa ccctggataa       660
cgccatgtat ggtcatagct g                                                 681
```